US006051405A

United States Patent [19]
FitzGerald et al.

[11] Patent Number: 6,051,405
[45] Date of Patent: Apr. 18, 2000

[54] CONSTRUCTS ENCODING RECOMBINANT ANTIBODY-TOXIN FUSION PROTEINS

[75] Inventors: David FitzGerald, Silver Spring; Vijay Kumar Chaudhary, Rockville; Ira Harry Pastan, Potomac; Thomas Alexander Waldmann, Silver Spring, all of Md.; Cary L Queen, Palo Alto, Calif.

[73] Assignees: The United States of America as represented by the Secretary of the Department of Health and Human Services, Washington, D.C.; Protein Design Labs, Inc., Fremont, Calif.

[21] Appl. No.: 07/865,722

[22] Filed: Apr. 8, 1992

Related U.S. Application Data

[63] Continuation of application No. 07/341,361, Apr. 21, 1989, abandoned, and a continuation-in-part of application No. 06/911,227, Sep. 24, 1986, Pat. No. 4,892,827.

[51] Int. Cl.[7] .................................................... C07K 16/46
[52] U.S. Cl. ............................................. 435/69.7; 435/91
[58] Field of Search ................................... 435/91, 320.1, 435/317.1, 252.33, 252.3, 240.2, 70.1, 69.7, 69.1, 91.1, 91.4, 91.41, 325, 326, 328, 330, 455; 536/27, 27.1; 935/10, 15, 27; 530/387.3; 514/44

[56] References Cited

U.S. PATENT DOCUMENTS

| | | | |
|---|---|---|---|
| 4,545,985 | 10/1985 | Pastan et al. | 424/180.1 |
| 4,675,382 | 6/1987 | Murphy, Jr. | 530/350 |
| 4,867,962 | 9/1989 | Abrams | 424/1.49 |
| 4,892,827 | 1/1990 | Pastan et al. | 435/63 |
| 4,894,443 | 1/1990 | Greenfield et al. | 424/179.1 |

OTHER PUBLICATIONS

Willaims, G. 1988 TIBTECH. 6,36–42.
Chaudhary et al. 1989. Nature 339, 394–397.
Vitteta et al. 1987. Science. 238, 1098–1104.
Chaudhary et al. 1988. Proc. Nat'l. Acad. Sci. USA. 85, 2939–2943.
Hwang et al. 1987. Cell. 48, 127–136.
Seigall et al. 1988 Proc. Nat'l. Acad. Sci. USA 85, 9738–9742.
Lorderbaum–Galski et al. 1988. Proc. Nat'l. Acad Sci. USA. 85, 1922–1926.
Kelley et al., 85 *Proc. Nat'l. Acad. Sci. USA* 3980–2984 (1988).

*Primary Examiner*—Christopher S. E. Low
*Attorney, Agent, or Firm*—Townsend and Townsend and Crew LLP

[57] ABSTRACT

The present invention describes constructs encoding recombinant scFv-toxin fusion proteins which selectively kill cells bearing appropriate antigens or receptors.

9 Claims, 6 Drawing Sheets

VK73  5' GCAGGTGTCCACTCCATATGCAGGTCCAGTCCAGCAGTCTGGG 3'
               NdeI
                    KpnI
VK74  5' CACACACAGGGGCCAGTGGTACCCGCCCCGAGCCACCGCCT 3'

VK75  5' CTTCCTGCTAATCAGTGCCGGCTGGGGTGGGCGGGGCTCT 3'
                              KpnI
      CAAATTGTTCTTCTCACCCAGTCTCC 3'

VK76  5' GAAGATGGATCACAGTTGGTGAATTCATTAAGCTTTGAGCTCCAGCTTG 3'
                                        HindIII
      GTCCCCAGAACC 3'

FIG. 1B.

CONSTRUCTS ENCODING RECOMBINANT ANTIBODY-TOXIN FUSION PROTEINS

This is a Continuation of application Ser. No. 07/341,361 filed Apr. 21, 1989, now abandoned which is a continuation-in-part of Ser. No. 06/911,227 filed Sept. 24, 1986, which is now U.S. Pat. No. 4,892,827.

This is a continuation-in-part of pending application Ser. No. 06/911,227 filed Sep. 24, 1986, which is incorporated herein by reference. The parent application (06/911,227) teaches the production of recombinant proteins from modified Pseudomonas exotoxin (PE) gene fused with DNA sequences encoding a recognition protein for which a specific receptor exists on the cells. The PE gene was modified to achieve alteration of specific segments or sequences of various domains of the PE molecule. This was exemplified in the parent application with the construction and expression of an IL-2-PE fusion gene. The present application relates to the production of improved toxins utilizing PE, and more particularly, to the synthesis of recombinant antibody-toxin fusion proteins which are capable of effectively and selectively killing cells bearing appropriate antigens or receptors. The work described herein was partially supported by the U.S. Government.

BRIEF DESCRIPTION OF THE DRAWINGS

Various objects, features and many of the attendant advantages of the invention will be better understood upon a reading of the following detailed description when considered in connection with the accompanying drawings wherein:

FIG. 1(b) shows the oligonucleotides used for polymerase chain reaction (PCR) with VK074, VK075 and VK076 each shown on two lines. Portions of VK073 and VK075 are complimentary to the noncoding strands of heavy and light chain cDNA, while that of VX074 and VK076 are complimentary to the coding strands of heavy and light chain cDNAs, respectively. VK073 and VK074 were used for amplifying $V_H$ segment using anti-Tac heavy chain cDNA while VK075 and VK076 were used to generate $V_L$ segment using anti-Tac light chain cDNA as shown in FIG. 1a. All the oligonucleotides have been written in 5' to 3' direction. Sequences complimentary to coding or noncoding strands of $V_L$ or $V_H$ cDNAs are shown in plain boxes. Sequences encoding peptide linker between $V_H$ and $V_L$ are underlined with a broken line.

DETAILED DESCRIPTION OF THE INVENTION

Figure 1A:
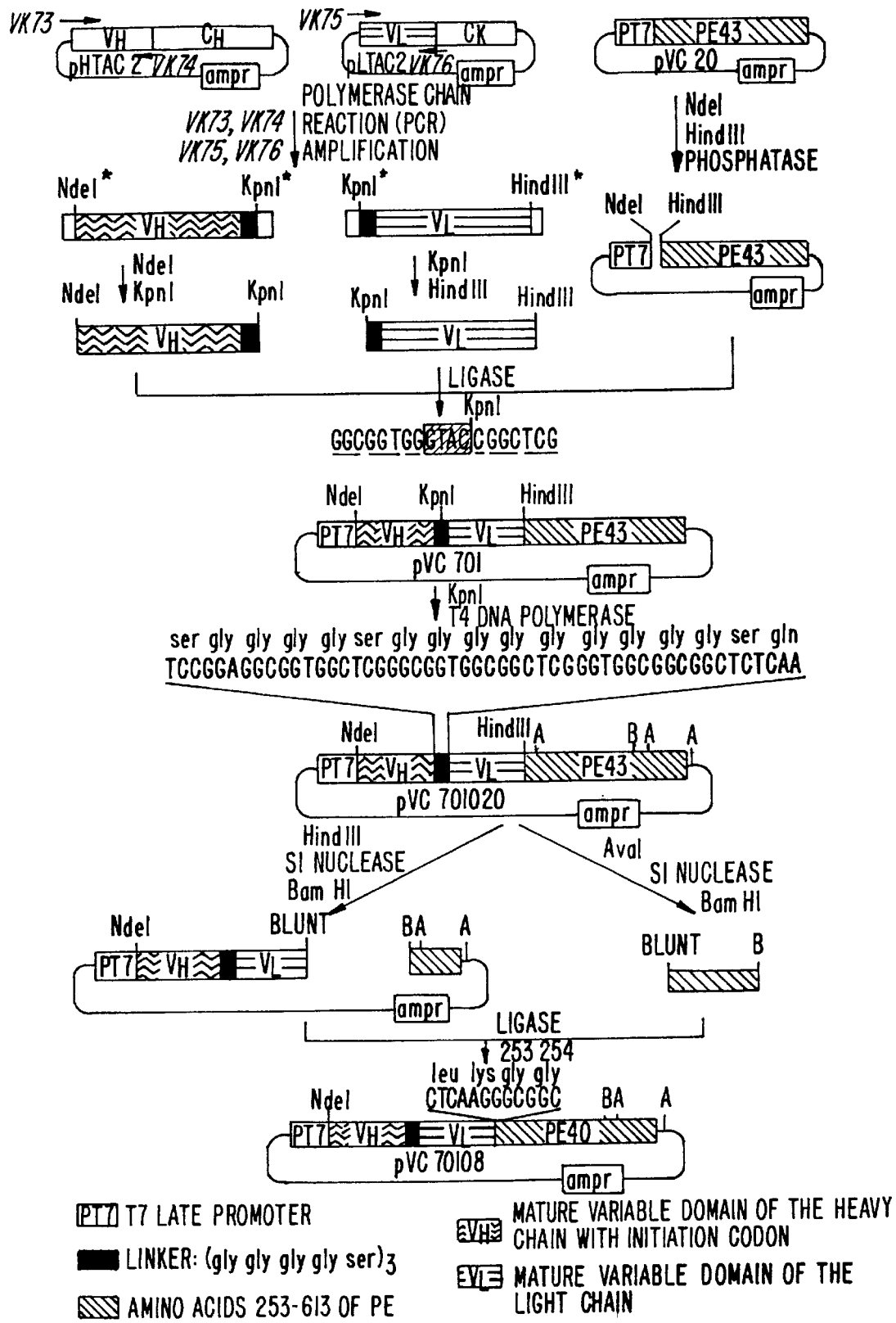
FIG. 1(a) illustrates a schematic construction of expression plasmid pVC70108. Plasmid pVC70108 contains a fusion gene encoding various domains of anti-Tac: $V_H$-variable domain of the heavy chain (first 116 amino acids of mature heavy chain), 15 amino acid linker [(gly-gly-gly-gly-ser)$_3$], $V_L$-variable domain of the light chain (first 106 amino acids of mature light chain) and amino acids 253–613 of PE, which possesses translocating and ADP ribosylating activity, as a single polypeptide chain. The encoded protein is called an antibody-toxin fusion protein or more specifically anti-Tac(Fv)-PE40. The fusion gene is under control of a T7 promoter linked to Shine-Delgarno region and initiation codon (PT7). E. coli strain BL21 (λDE3) carrying pVC70108 was used to express hybrid protein upon IPTG induction. Amp$^r$, β lactamase gene; B. BamHI, A, AvaI. Oligonucleotides used for PCR have been shown as horizontal arrows. In plasmid pVC701, four extra bases have been shown in a hatched box.

A recombinant immunotoxin in accordance with the present invention comprises an antibody-PE40 recombinant fusion protein. The recombinant fusion protein is produced by an expression vector or plasmid comprising DNA segments which direct the synthesis of said fusion protein. A composition comprises an effective amount of an antibody-PE40 recombinant fusion protein to kill cells bearing a receptor or an antigen to which the antibody binds, and a pharmaceutically acceptable carrier. A method for achieving targeted cytotoxicity, comprises contacting cells targeted to be killed with a cytotoxic amount of the composition of antibody-PE40 recombinant fusion protein, said targeted cells being those having receptors or antigens to which said antibody binds, but the composition being without significant cytotoxicity to cells which lack receptors or antigens for the binding of said antibody (Table 2).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art. The materials, methods and examples are only illustrative and not limiting.

The term "antibody" as used herein means a portion of an immunoglobulin molecule (see W. E. Paul, ed.. "Fundamental Immunology," Raven Press, N.Y., 1984, pp. 131–165) capable of binding to an antigen. According to this definition, the term "antibody" includes various forms of modified or altered antibodies, such as an intact immunoglobulin, an Fv fragment containing only the light and heavy chain variable regions, an Fab or (Fab)$'_2$ fragment containing the variable regions and parts of the constant regions, a single-chain (SC) antibody (Bird et al., 1988, *Science* 242, 424–426; Huston et al., 1988, *Proc. Nat. Acad. Sci. USA* 85, 5879–5883), and the like. The antibody may be of animal (especially mouse or rat) or human origin or may be chimeric (Morrison et al., 1984, *Proc. Nat. Acad. Sci. USA* 81, 6851–6855) or humanized (Jones et al., 1986, *Nature* 321, 522–525, and published UK patent application #8707252). Methods of producing antibodies suitable for use in the present invention are well known to those skilled in the art and can be found described in such publications as Harlow & Lane, Antibodies: A Laboratory Manual, Cold Spring Harbor Laboratory, 1988. The genes encoding the antibody chains may be cloned in cDNA or in genomic form by any cloning procedure known to those skilled in the art. See for example Maniatis et al., Molecular Cloning: A Laboratory Manual, Cold Spring Harbor laboratory, 1982. The term "without significant cytotoxicity" as used herein means that the fusion protein of the present invention does not affect the function of the untargeted cells to any appreciable degree or to any abnormal level.

The recombinant antibody-PE40 fusion protein may be composed of one or two polypeptide chains. The production of a single chain fusion protein has been illustrated herein. To produce two chain fusion proteins, no amino acid linker would be inserted between the $V_H$ and $V_L$ sequences. Instead a termination codon would be inserted after the $V_H$ sequence, and an initiation codon and ribosome binding sequence would be inserted before the $V_L$ sequence. In another embodiment of the invention, the $V_L$ and $V_H$ sequences will be followed respectively by part or all of the light and heavy chain constant regions, e.g., the whole kappa light chain constant region and the $C_H1$ domain of the heavy chain constant region, with or without the heavy chain hinge domain. The $V_L$, $V_H$ and PE40 genes may occur in any order on the plasmid, hence the PE40 gene may be attached to either the 5' or 3' end of either the light or heavy chain gene. Those skilled in the art will realize that additional modifications, deletions, insertions and the like may be made to the antibody and PE40 genes. Especially, deletions or changes may be made in PE40 or in the linker connecting the antibody gene to PE40, in order to increase cytotoxicity of the fusion protein toward target cells or to decrease nonspecific cytotoxicity toward cells without antigen for the antibody. All such constructions may be made by methods of genetic engineering well known to those skilled in the art (see, generally, Maniatis et al., supra) and may produce proteins that have differing properties of affinity, specificity, stability and toxicity that make them particularly suitable for various clinical or biological applications.

In the example disclosed herein, the $V_L$, $V_H$, and PE40 genes are contained on a single plasmid. Moreover the recombinant antibody-PE40 protein after synthesis remains internal to the *E. coli* host cell until purified. In another embodiment of the invention, the $V_L$ gene and any light chain constant region will be on one plasmid; while the $V_H$ gene, any heavy chain constant region, and the PE40 gene will be on a second plasmid. In either case, the $V_L$ and/or $V_H$ genes may be preceded by a signal sequence that directs the secretion of the recombinant fusion protein from the cell (Better et al., 1988, *Science* 240, 1041–1043; Skerra & Pluckthun, 1988, *Science* 240, 1038–1041).

The fusion proteins of the invention may be expressed in a variety of host cells, including *E. coli,* other bacterial hosts, yeast, and various higher eucaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eucaryotic cells, the control sequences will include a promoter and preferably an enhancer derived from immunoglobulin genes, SV40, cytomegalovirus, etc., and a polyadenylation sequence, and may include splice donor and acceptor sequences. The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, "Protein Purification", Springer-Verlag, N.Y. (1982)). Substantially pure compositions of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or otherwise, such as in developing and performing assay procedures. (See, generally, *Immunological Methods,* Vols. I and II, Lefkovits and Pernis, eds., Academic Press, New York, N.Y. (1979 and 1981)).

The recombinant fusion proteins and pharmaceutical compositions of this invention are particularly useful for parenteral administration, i.e., subcutaneously, intramuscularly or intravenously. The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate and the like. The concentration of fusion protein in these formulations can vary-widely, i.e., from less than about 0.5%, usually at or at least about 1% to as much as 15 or 20% by weight and will be selected primarily based on fluid volumes, viscosities, body weight and the like in accordance with the particular mode of administration selected.

Thus, a typical pharmaceutical composition for intramuscular injection may comprise 1 ml sterile buffered water, and 10 mg of fusion protein. A typical composition for intravenous infusion may comprise 250 ml of steril Ringer's solution, and 10 mg of protein. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980), which is incorporated herein by reference.

The compositions containing the present fusion proteins or a cocktail thereof (i.e., with other proteins) can be administered for prophylactic and/or therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

In prophylactic applications, compositions containing the present antibodies or a cocktail thereof are administered to a patient not already in a disease state to prevent the onset of disease. Such an amount is defined to be a "prophylactically effective dose." In this use, the precise amounts again depend upon the patient's state of health and general level of immunity.

Single or multiple administrations of the compositions may be administered depending on the dosage and frequency as required and tolerated by the patient. In any event, the composition should provide a sufficient quantity of the proteins of this invention to effectively treat the patient.

Among various uses of the recombinant fusion proteins of the present invention are included a variety of disease conditions caused by specific human cells that may be eliminated by the toxic action of the protein. One preferred application is the treatment of autoimmune conditions such as graft-versus-host disease, organ transplant rejection, type I diabetes, multiple sclerosis, rheumatoid arthritis, systemic lupus erythematosus, myasthenia gravis and the like caused by T and B cells. The example disclosed herein is illustrative. Another preferred application is for the treatment of cancer, caused by malignant cells of various types. The fusion proteins may also be used in vitro, for example in the elimination of harmful cells from bone marrow before transplant. The antibody portion of the fusion protein is chosen according to the intended use. Proteins on the membranes of T cells that may serve as targets for the antibody include CD2 (T11), CD3. CD4 and CD8. Proteins found predominantly on B cells that might serve as targets include CD10 (CALLA antigen), CD19 and CD20. CD45 is a possible target that occurs broadly on lymphoid cells. These and other possible target lymphocyte antigens for the antibody are described in Leucocyte Typing III, A. J. McMichael, ed., Oxford University Press, 1987. Antigens found on cancer cells that may serve as targets for the antibody include carcinoembryonic antigen (CEA), the transferrin receptor, P-glycoprotein, c-erbB2, and antigens described in the Abstracts of the Third International Conference on Monoclonal Antibody Immunoconjugates for Cancer (San Diego, Ca. 1988). Those skilled in the art will realize that antibodies may be chosen that bind to antigens expressed on still other types of cells, for example membrane glycoproteins or growth factor or hormone receptors such as epidermal growth factor receptor and the like.

MATERIALS AND METHODS

The following example is offered by way of illustration, not limitation.

Construction of Expression Plasmid for Anti-Tac (Fv)-PE40

A plasmid designated herein as pVC70108 was assembled such that it contained an ATG encoding an initiating methionine, a 348 bp DNA segment encoding anti-Tac $V_H$ joined to a 318 bp DNA segment encoding $V_L$ through a 45 bp linker; $V_L$ was in turn joined to a DNA segment encoding amino acids 253–613 of PE (FIG. 1). The complete sequences of the $V_H$–$V_L$-linker-PE40 DNA segment and of the encoded anti-Tac (Fv)-PE40 fusion protein are presented in Table 1.

As shown in FIG. 1a and 1b, two sets of oligonucleotides were used in polymerase chain reaction (PCR) based amplification (using Gene Amp kit, Perkin Elmer Cetus) to create the following:

(a) NdeI site at the 5' end of $V_H$ gene, $V_H$ domain and first amino terminal nine codons of the linker followed by a KpnI site (using VK073 and VK074 with antiTac heavy chain cDNA in plasmid pHTac2).

(b) Seven carboxy terminal codons of the peptide linker with a KpnI site, $V_L$ domain and a HindIII site at the 3' end of gene encoding $V_L$ (using VK075 and VK076 with light chain cDNA in plasmid pLTac2).

Plasmids carrying full length cDNAs, encoding heavy and light chains of antiTac, as EcoRI inserts in pUC18 were used as template. After PCR amplification, two fragments: (1) 413 bp fragment containing variable domain of the heavy chain, and amino terminal part of the peptide linker; (2) a 396 bp fragment containing carboxy terminal part of the peptide linker and variable domain of light chain, were isolated. 413 bp fragment was cut with NdeI and KpnI to yield a 377 bp fragment. 396 bp fragment was restricted with KpnI and HindIII to produce a 340 bp fragment. Separately plasmid pVC20, carrying gene encoding a PE derivative PE43 (Chaudhary et al, *Proc. Natl. Acad. Sci. USA*, 85:2939–2943, 1988), was restricted with NdeI and HindIII and dephosphorylated to isolate a 3.75 Kb fragment. This was then ligated with 377 bp and 340 bp fragments isolated earlier. The resultant plasmid pVC701 contains a fusion gene under T7 promoter. This gene contains four extra bases in the peptide linker. Plasmid pVC701 was cut with KpnI, treated with T4 DNA polymerase to remove 3' overhangs and ligated to isolated plasmid pVC701020. pVC701020 (4.4. Kb) encodes a fusion protein comprised of variable domains of antiTac and PE43.

pVC701020 was restricted with HindIII, treated with SI nuclease to remove 5' overhangs, cut with BamHI and dephosphorylated to isolate a 3.65 Kb fragment. Separately, pVC701020 was cut with AvaI, treated with SI nuclease and cut with BamHI to isolate a 750 bp fragment. 3.65 Kb and 750 bp fragments were ligated together to generate a plasmid pVC70108. pVC70108 carries a fusion gene encoding $V_H$ linked to $V_L$ through a 15 amino acid linker, and $V_L$ linked to amino acids 253 to 613 of PE. A methionine codon has been created at the 5' end of $V_H$.

As noted earlier, the assembled gene is under the control of a T7 promoter. The authenticity of the coding region of the plasmid was confirmed by DNA sequencing (data not shown).

A deposit of plasmid pVC70108 has been made at the ATCC, Rockville, Md. on Mar. 31, 1989 under the accession number 67913. The deposit shall be viably maintained, replacing if it becomes non-viable, for a period of 30 years from the date of the deposit, or for 5 years from the last date of request for a sample of the deposit, whichever is longer, and made available to the public upon issuance of a patent from this application, without restriction, in accordance with the provisions of the law. The Commissioner of Patents and Trademarks, upon request, shall have access to the deposit.

Purification and Characterization of Anti-Tac(Fv)-PE40

Figure 2A:
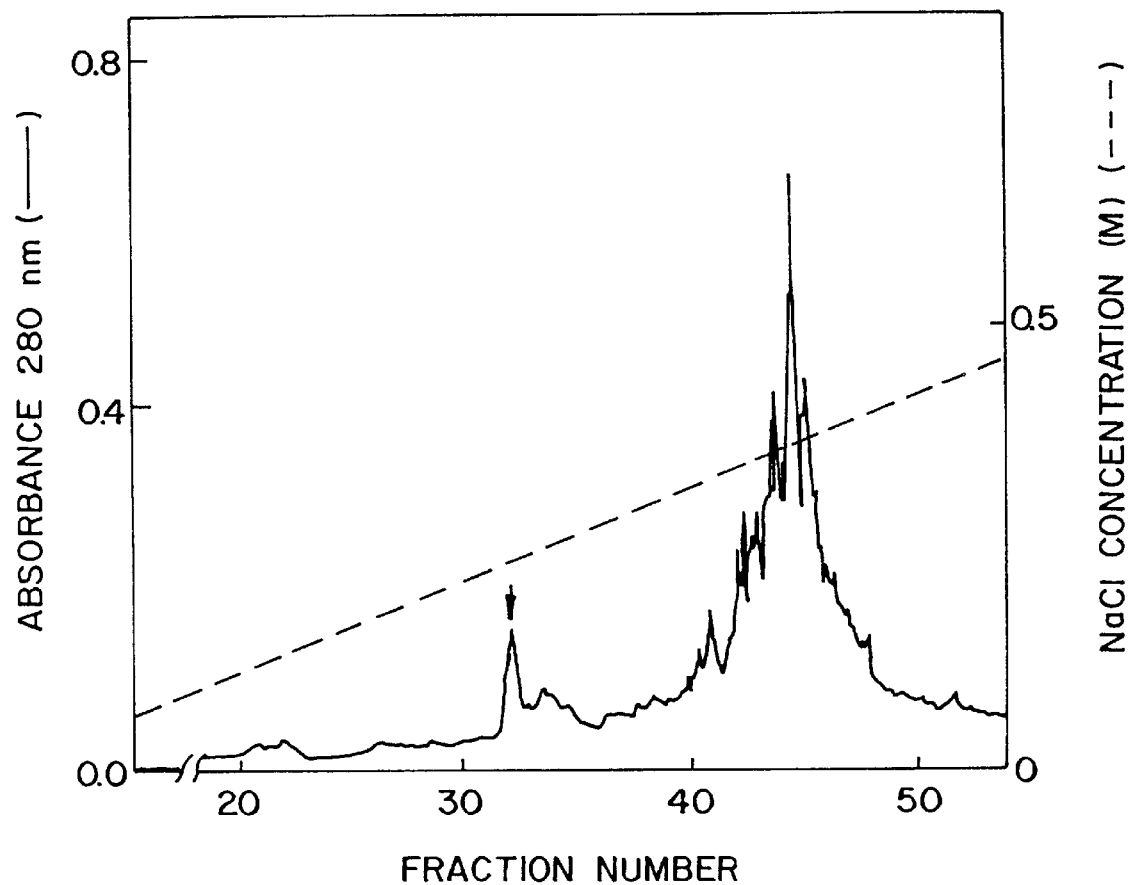
FIG. 2(a) shows the results of purification of renatured soluble anti-Tac(Fv)-PE40 by Mono Q column chromatography. Renatured material was applied on a Mono Q column; proteins were eluted with a NaCl gradient (0–0.5M) and 4 ml fractions were collected. The position of active monomeric anti-Tac(Fv)-PE40 is shown by a vertical arrow.
Figure 2B:
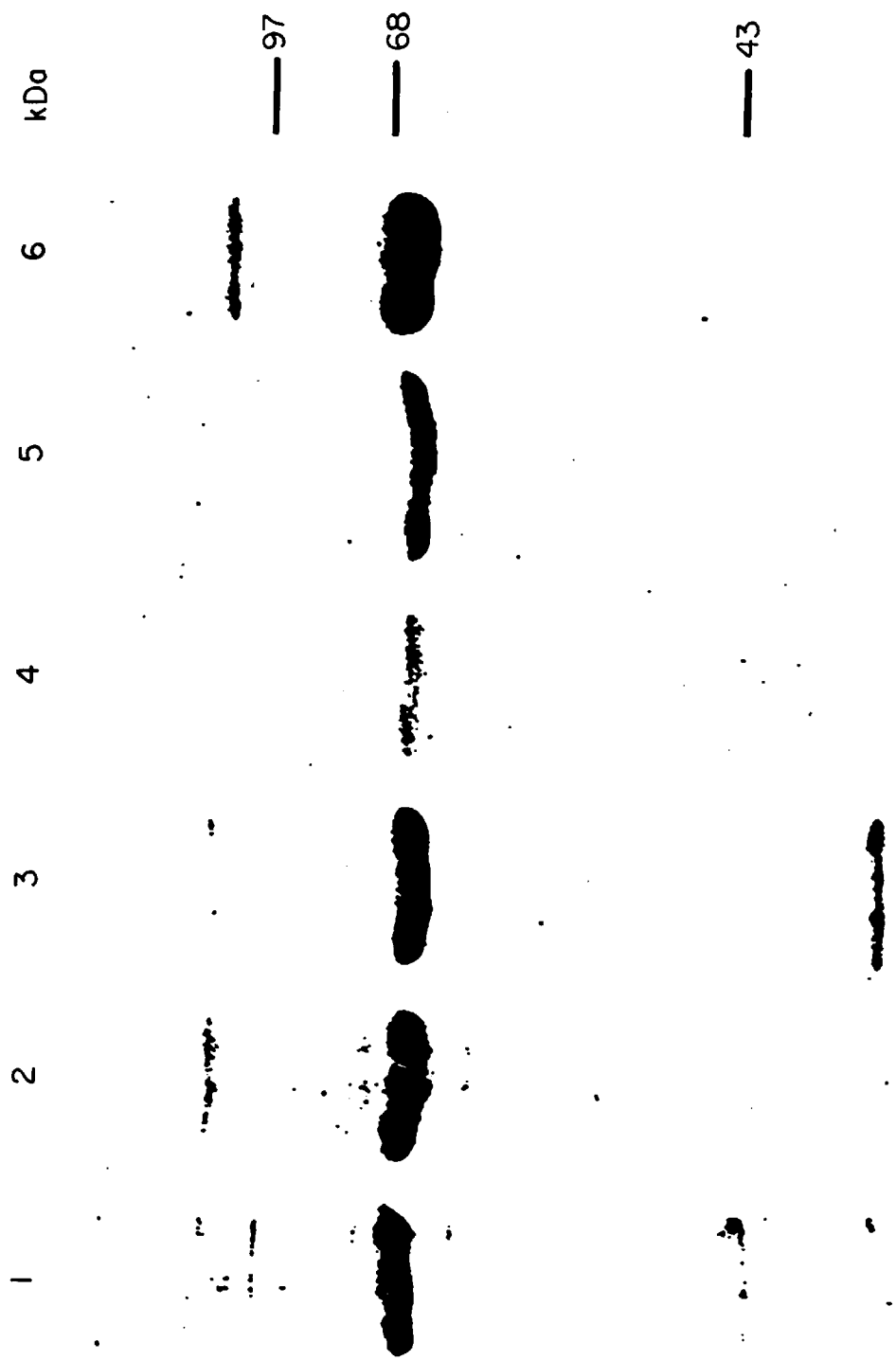
FIG. 2(b) shows the results of SDS-PAGE of samples at various stages of purification. The gel was stained with Coomassie blue. Lane 1, total cell pellet; lane 2, spheroplasts; lane 3, 100,000 xg pellet of sonicated spheroplasts; lane 4, pool of fractions (32–33) from the Mono Q column; lane 5, pool of peak fractions from the TSK-250 column; lane 6, native PE, Mr 66 kDa. Molecular weight markers are on the side with Mr in kDa.

Upon IPTG induction, *E. coli* strain BL21 (λADE3) carrying plasmid p70108 produced large amounts of a protein of approximately 65 kDa, as shown by SDS PAGE (lane 1, FIG. 2b). On immunoblots, the 65 kDa chimeric protein reacted with an antibody to PE (data not shown). The fusion protein was mostly contained in the 100,000 xg pellet (lane 3, FIG. 2b) of the sonicated spheroplasts (lane 2, FIG.

2b). This pellet was used as the source to prepare anti-Tac (Fv)-PE40. The technique of guanidine hydrochloride denaturation followed by rapid dilution was used to solubilize and renature the chimeric protein (Chaudhary et al, 1988, Nature 335, 369–372; Siegall et al, 1988, Proc. Natl. Acad. Sci. USA 85, 9738–9742). DTT was omitted from the denaturation buffer and renaturation was carried out for 16 hours. After renaturation and dialysis, the sample was applied to a Mono Q column (HR 10/10) at 3 ml/min. The column was washed with 40 ml Buffer A (20 mM Tris-HCl, pH 7.6) and developed with a 200 ml linear gradient (0–0.5M NaCl). Eluted proteins were monitored at 280 nm. Fractions (4 ml) were collected and tested for cytotoxicity on HUT-102 cells. For SDS-PAGE, samples were boiled with Laemmli sample buffer and electrophoresed on a 10% gel. The monomeric form of the fusion protein eluted at 0.2–0.22M NaCl (FIG. 2b, lane 4 and FIG. 2a). High molecular weight aggregates were eluted at higher ionic strength (Fractions 42–50, FIG. 2a). Further purification of the chimeric protein was carried out on a TSK-250 gel filtration column; the chimeric protein eluted as a symmetrical peak at the location expected for a 65 kDa protein (data not shown). SDS-PAGE showed the protein to be >95% pure (lane 5, FIG. 2b) and N-terminal amino acid sequence analysis showed the protein had the expected N-terminal sequence, met, gln, val-. About 200 μg of highly purified monomeric single chain anti-Tac(scFv)-PE40 was obtained from 1 liter of cells grown to an $OD_{650}$ of 0.6 before induction.

Testing Cytotoxicity of Anti-Tac(Fv)-PE40

HUT-102 cells were washed twice with serum free medium and plated in RPMI 1640 medium with 5% fetal bovine serum at $3 \times 10^5$ cells/well in 24-well plates. Various dilutions of anti-Tac(Fv)-PE40 were prepared in PBS with 0.2% human serum albumin and added to appropriate wells. After 20 hours the cells were labeled with $^3$H-leucine for 90 min and the radioactivity in the TCA precipitate of the cell pellet determined. The results are expressed as % of control with no toxin added. For competition, 10 μg of anti-Tac or OVB3 were added to each well just before adding anti-Tac (Fv)-PE40.

Competition Binding Analysis of Anti-Tac(Fv)-PE40

I-125 labeled anti-Tac (2 μCi/μg) as tracer was used at 1.5 ng per assay with varying concentrations of competitor and $4 \times 10^6$ HUT-102 cells as source of Tac antigen in 0.2 ml of binding buffer (RPMI 1640 with 10% fetal bovine serum, 100 μg/ml human IgG, 0.1% sodium azide), and incubated at room temperature (22°–24° C.) with mixing for 2 hours. Under these conditions, the concentration of tracer is 50 pM and Tac peptide 500 pM. Free tracer is 10 pM by calculation and satisfies the condition that free tracer be less than $1/Ka=100$ pM (using $10^{10}$ $M^{-1}$ for anti-Tac Ka) for the assumptions of the competition analysis. Assays were performed in parallel with a control cold anti-Tac antibody, and curve shifts at the 50% inhibition point of bound/free tracer binding (Ro/2) versus log competitor concentration were quantitated. The concentrations were obtained from the antilogs of the abscissa, and the affinity constant Kx for the construct, X, derived from the formula (Berzofsky et al, 1981, Molec. Immunol 18, 751–763)

$$([X]_{1/2}-[anti-Tac]_{1/2})=1/Kx-1/Ka$$

where $[X]_{1/2}$ indicates the concentration of competitor at which tracer binding is Ro/2. Standard Scatchard plotting of binding data with anti-Tac gave linear graphics and a Ka of $9.7 \times 10^9$ $M^{-2}$, comparable to that obtained by other investigators (Robb et al, 1984, J. Exp. Med. 160, 1126–1146). The Ka of $3.5 \times 10^9 M^{-1}$ for anti-Tac(Fv)-PE40 was calculated from the above formula. All concentrations were measured by Bradford protein microassay against a standard curve with human IgG. For competition analysis, these concentrations were normalized on the basis of the bindable fraction obtained in separate tests with radiolabeled anti-Tac (Fv)-PE40 (0.44) and radiolabeled anti-Tac (0.8) with excess HUT-102 cells to yield concentrations of bindable protein for the abscissa.

Selective cytotoxicity of anti-Tac(Fv)-PE40

Figure 3:
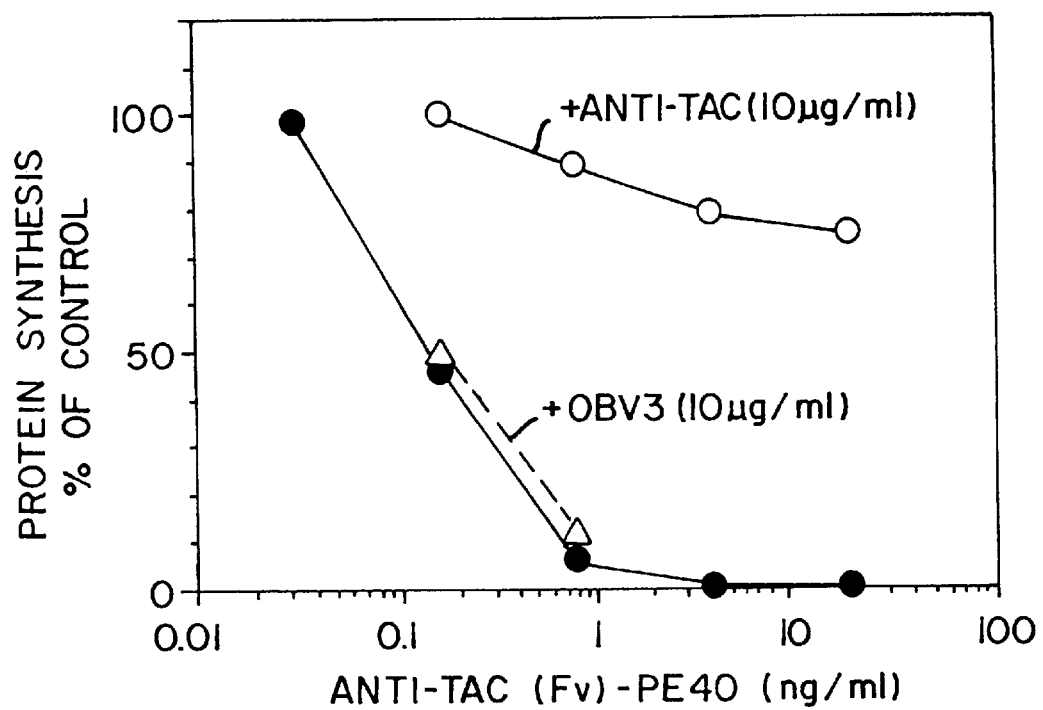
FIG. 3 shows the results of a cytotoxicity study of anti-Tac(Fv)-PE40 on HUT-102 cells expressing IL2 receptors. Cytotoxicity of anti-Tac(Fv)-PE40 on HUT-102 cells was determined by measuring protein synthesis with (·) anti-Tac(Fv)-PE40; (o) anti-Tac(Fv)-PE40+10 μg anti-Tac; (Δ) anti-Tac(Fv)-PE40+10 μg OVB3.

Since the anti-Tac antibody binds to the p55 subunit (Tac antigen) of the IL-2 receptor, which is present in large amounts on HUT-102 cells (Uchiyama et al, 1981, J. Immunol. 126, 1393–1397), the chimeric protein was initially tested for cytotoxicity on HUT-102 cells, as described above. Anti-Tac(Fv)-PE40 inhibited protein synthesis in a dose-dependent manner with an $ID_{50}$ of 0.15 ng/ml ($2.3 \times 10^{-12}M$) in a 20 hour assay (FIG. 3 and Table 2). At concentrations of more than 4 ng/ml, there was complete inhibition of protein synthesis. Several specificity controls were carried out. Addition of excess anti-Tac (10 μg/ml) prevented the cytotoxicity of anti-Tac(Fv)-PE40 on HUT-102 cells, whereas a control monoclonal antibody, OVB3, directed against an antigen found on ovarian cancer cells did not (FIG. 3). Another human T cell line CrIl.2, which has lower number of IL2 receptors than HUT102, was also very sensitive to Anti-Tac(Fv)PE40 with an $ID_{50}$ of 2.7 ng/ml (Table 2). Furthermore, several human cell lines without IL2 receptors including the T-cell line. CEM, A431, KB and OVCAR-3 were not affected by anti-Tac(Fv)-PE40 even at 1 μg/ml (Table 2).

It has been reported that anti-Tac chemically conjugated to PE (anti-Tac-PE) or PE40 killed HUT102 cells (Kondo et al, 1988, J. Biol. Chem. 263, 9470–9475; FitzGerald et al, 1984, J. Clin. Invest. 74, 966–971). When thioether conjugates are made, Anti-TacPE has an $ID_{50}$ of about 1.2 ng/ml and anti-Tac-PE40 similarly prepared had an $ID_{50}$ of 13 ng/ml. Since anti-Tac(Fv)-PE40 (65 kDa) is about 30% of the molecular weight of anti-Tac-PE (216 kDa), the chimeric toxin of the present invention is on a molar basis several-fold more active than anti-Tac-PE and considerably more active than anti-Tac-PE40. The very high activity of anti-Tac(Fv)-PE40 on the target HUT102 cells, about 10-fold higher than the chemically prepared anti-Tac-PE40 or the recombinant fusion protein IL-2-PE40 (Lorberboum-Galski et al., 1988. Proc. Nat. Acad. Sci. USA 85, 1922–1926) is unexpected and could not have been predicted from prior art. It is especially unexpected that anti-Tac(Fv)-PE40 is more cytotoxic than any other IL-2-PE fusion protein because anti-Tac(Fv) antibody has a much lower affinity for the complete IL-2 receptor, $K_a=3.5 \times 10^9 M^{-1}$ as given above, than does IL-2, $K_a=10^{11}$ $M^{-1}$ (Tsudo et al., 1987, Proc. Nat. Acad. Sci. USA, 84, 5394–5398).

Figure 4:
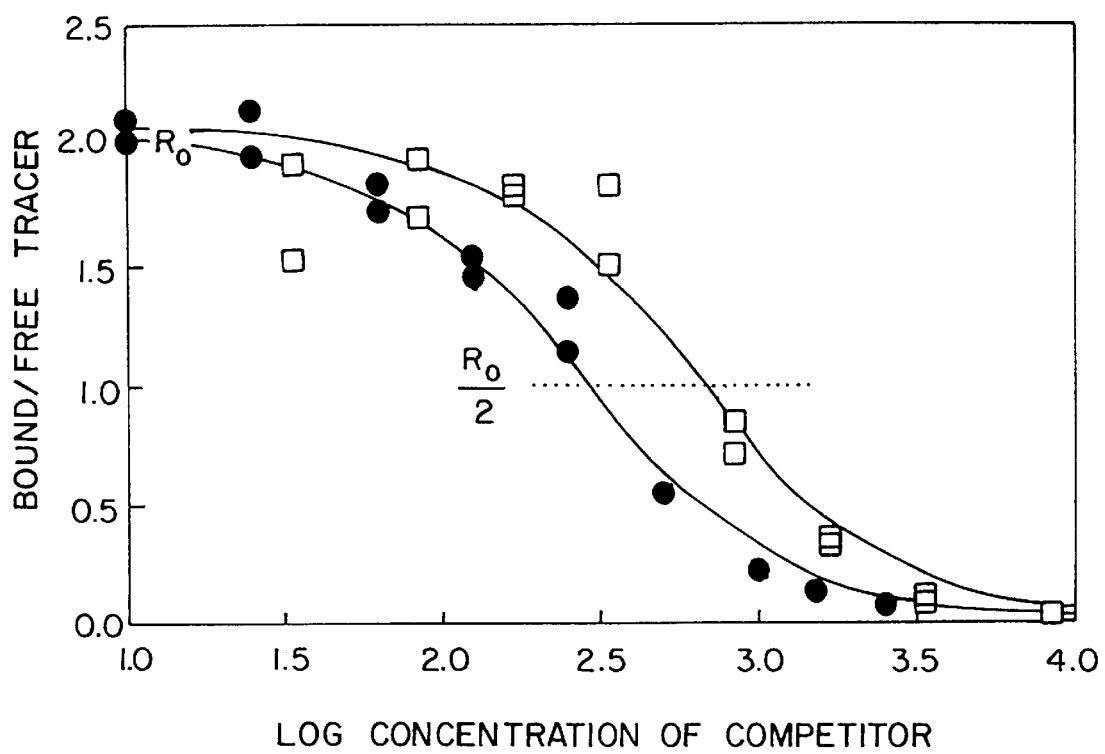
FIG. 4 shows a competition binding analysis of anti-Tac (Fv)-PE40. Competition data of anti-Tac(Fv)-PE40 (open squares) and native mouse anti-Tac antibody (solid circles) with I-125 labeled tracer anti-Tac antibody to bind to Tac antigen on HUT-102 cells is shown. Solid lines are computer generated idealized curves that model binding competition. $R_0$ is the bound/free ratio for tracer in the absence of competitor, and Ro/2 is the 50% inhibition point for tracer binding, from which a binding affinity of $3.5 \times 10^9$ M$^{-1}$ for anti-Tac(Fv)-PE40 is calculated, compared with $9.7 \times 10^9$ M$^{-1}$ for native anti-Tac.

Competition binding studies showed an affinity of $3.5 \times 10^9 M^{-1}$ for anti-Tac(Fv)-PE40, reduced approximately three-fold relative to that of anti-Tac, measured at $9.7 \times 10^9 M^{-1}$ (FIG. 4). This can be compared with a four-fold loss of affinity of an Fv construct versus Fab fragment of anti-bovine growth hormone (Bird et al, 1988, Science 242, 423≡426) and a six-fold loss for the Fv construct of anti-digoxin versus Fab fragment of antidigoxin (Houston et al, 1988, Proc. Natl. Acad. Sci. USA 85, 5879–5883).

The relative preservation of affinity by the Fv binding site is evidently superior with anti-Tac relative to that observed with anti-BGH and anti-digoxin antibodies.

In summary, the data presented herein clearly demonstrates the synthesis of an active recombinant immunotoxin in *E. coli* by fusion of cDNAs encoding the anti-Tac variable regions with a fragment of DNA encoding a modified form of *Pseudomonas* exotoxin. This accomplishment now enables the creation of similar active recombinant immunotoxins with other antibodies using *E. coli* or other expression vectors well known to one of ordinary skill in the art.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

Sequence Of Anti-Tac(Fv)-PE40

```
                          30                             60
ATGCAGGTCCAGCTGCAGCAGTCTGGGGCTGAACTGGCAAAACCTGGGGCCTCAGTGAAG
MetGlnValGlnLeuGlnGlnSerGlyAlaGluLeuAlaLysProGlyAlaSerValLys 90                            120
ATGTCCTGCAAGGCTTCTGGCTACACCTTTACTAGCTACAGGATGCACTGGGTAAAACAG
MetSerCysLysAlaSerGlyTyrThrPheThrSerTyrArgMetHisTrpValLysGln 150                            180
AGGCCTGGACAGGGTCTGGAATGGATTGGATATATTAATCCTAGCACTGGGTATACTGAA
ArgProGlyGlnGlyLeuGluTrpIleGlyTyrIleAsnProSerThrGlyTyrThrGlu 210                            240
TACAATCAGAAGTTCAAGGACAAGGCCACATTGACTGCAGACAAATCCTCCAGCACAGCC
TyrAsnGlnLysPheLysAspLysAlaThrLeuThrAlaAspLysSerSerSerThrAla 270                            300
TACATGCAACTGAGCAGCCTGACATTTGAGGACTCTGCAGTCTATTACTGTGCAAGAGGG
TyrMetGlnLeuSerSerLeuThrPheGluAspSerAlaValTyrTyrCysAlaArgGly 330                            360
GGGGGGGTCTTTGACTACTGGGGCCAAGGAACCACTCTCACAGTCTCCTCCGGAGGCGGT
GlyGlyValPheAspTyrTrpGlyGlnGlyThrThrLeuThrValSerSerGlyGlyGly
                                                            ↑
                         390                            420
GGCTCGGGCGGTGGCGGCTCGGGTGGCGGCGGCTCTCAAATTGTTCTCACCCAGTCTCCA
GlySerGlyGlyGlyGlySerGlyGlyGlyGlySerGlnIleValLeuThrGlnSerPro
                                                            ↑
                         450                            480
GCAATCATGTCTGCATCTCCAGGGGAGAAGGTCACCATAACCTGCAGTGCCAGCTCAAGT
AlaIleMetSerAlaSerProGlyGluLysValThrIleThrCysSerAlaSerSerSer 510                            540
ATAAGTTACATGCACTGGTTCCAGCAGAAGCCAGGCACTTCTCCCAAACTCTGGATTTAT
IleSerTyrMetHisTrpPheGlnGlnLysProGlyThrSerProLysLeuTrpIleTyr 570                            600
ACCACATCCAACCTGGCTTCTGGAGTCCCTGCTCGCTTCAGTGGCAGTGGATCTGGGACC
ThrThrSerAsnLeuAlaSerGlyValProAlaArgPheSerGlySerGlySerGlyThr 630                            660
TCTTACTCTCTCACAATCAGCCGAATGGAGGCTGAAGATGCTGCCACTTATTACTGCCAT
SerTyrSerLeuThrIleSerArgMetGluAlaGluAspAlaAlaThrTyrTyrCysHis 690                            720
CAAAGGAGTACTTACCCACTCACGTTCGGTTCTGGGACCAAGCTGGAGCTCAAGGGCGGC
GlnArgSerThrTyrProLeuThrPheGlySerGlyThrLysLeuGluLeuLysGlyGly
                                                            ↑
                         750                            780
AGCCTGGCCGCGCTGACCGCGCACCAGGCTTGCCACCTGCCGCTGGAGACTTTCACCCGT
SerLeuAlaAlaLeuThrAlaHisGlnAlaCysHisLeuProLeuGluThrPheThrArg 810                            840
CATCGCCAGCCGCGCGGCTGGGAACAACTGGAGCAGTGCGGCTATCCGGTGCAGCGGCTG
HisArgGlnProArgGlyTrpGluGlnLeuGluGlnCysGlyTyrProValGlnArgLeu 870                            900
GTCGCCCTCTACCTGGCGGCGCGGCTGTCGTGGAACCAGGTCGACCAGGTGATCCGCAAC
ValAlaLeuTyrLeuAlaAlaArgLeuSerTrpAsnGlnValAspGlnValIleArgAsn 930                            960
GCCCTGGCCAGCCCCGGCAGCGGCGGCGACCTGGGCGAAGCGATCCGCGAGCAGCCGGAG
AlaLeuAlaSerProGlySerGlyGlyAspLeuGlyGluAlaIleArgGluGlnProGlu 990                           1020
CAGGCCCGTCTGGCCCTGACCCTGGCCGCCGCCGAGAGCGAGCGCTTCGTCCGGCAGGGC
GlnAlaArgLeuAlaLeuThrLeuAlaAlaAlaGluSerGluArgPheValArgGlnGly
```

TABLE 1-continued

Sequence Of Anti-Tac(Fv)-PE40

```
                    1050                              1080
ACCGGCAACGACGAGGCCGGCGCGGCCAACGCCGACGTGGTGAGCCTGACCTGCCCGGTC
ThrGlyAsnAspGluAlaGlyAlaAlaAsnAlaAspValValSerLeuThrCysProVal 1110                              1140
GCCGCCGGTGAATGCGCGGGCCCGGCGGACAGCGGCGACGCCCTGCTGGAGCGCAACTAT
AlaAlaGlyGluCysAlaGlyProAlaAspSerGlyAspAlaLeuLeuGluArgAsnTyr 1170                              1200
CCCACTGGCGCGGAGTTCCTCGGCGACGGCGGCCACGTCAGCTTCAGCACCCGCGGCACG
ProThrGlyAlaGluPheLeuGlyAspGlyGlyAspValSerPheSerThrArgGlyThr 1230                              1260
CAGAACTGGACGGTGGAGCGGCTGCTCCAGGCGCACCGCCAACTGGAGGAGCGCGGCTAT
GlnAsnTrpThrValGluArgLeuLeuGlnAlaHisArgGlnLeuGluGluArgGlyTyr 1290                              1320
GTGTTCGTCGGCTACCACGGCACCTTCCTCGAAGCGGCGCAAAGCATCGTCTTCGGCGGG
ValPheValGlyTyrHisGlyThrPheLeuGluAlaAlaGlnSerIleValPheGlyGly 1350                              1380
GTGCGCGCGCGCAGCCAGGACCTCGACGCGATCTGGCGCGGTTTCTATATCGCCGGCGAT
ValArgAlaArgSerGlnAspLeuAspAlaIleTrpArgGlyPheTyrIleAlaGlyAsp 1410                              1440
CCGGCGCTGGCCTACGGCTACGCCCAGGACCAGGAACCCGACGCACGCGGCCGGATCCGC
ProAlaLeuAlaTyrGlyTyrAlaGlnAspGlnGluProAspAlaArgGlyArgIleArg 1470                              1500
AACGGTGCCCTGCTGCGGGTCTATGTGCCGCGCTCGAGCCTGCCGGGCTTCTACCGCACC
AsnGlyAlaLeuLeuArgValTyrValProArgSerSerLeuProGlyPheTyrArgThr 1530                              1560
AGCCTGACCCTGGCCGCGCCGGAGGCGGCGGGCGAGGTCGAACGGCTGATCGGCCATCCG
SerLeuThrLeuAlaAlaProGluAlaAlaGlyGluValGluArgLeuIleGlyHisPro 1590                              1620
CTGCCGCTGCGCCTGGACGCCATCACCGGCCCCGAGGAGGAAGGCGGGCGCCTGGAGACC
LeuProLeuArgLeuAspAlaIleThrGlyProGluGluGluGlyGlyArgLeuGluThr 1650                              1680
ATTCTCGGCTGGCCGCTGGCCGAGCGCACCGTGGTGATTCCCTCGGCGATCCCCACCGAC
IleLeuGlyTrpProLeuAlaGluArgThrValValIleProSerAlaIleProThrAsp 1710                              1740
CCGCGCAACGTCGGCGGCGACCTCGACCCGTCCAGCATCCCCGACAAGGAACAGGCGATC
ProArgAsnValGlyGlyAspLeuAspProSerSerIleProAspLysGluGlnAlaIle

1770
AGCGCCCTGCCGGACTACGCCAGCCAGCCCGGCAAACCGCCGCGCGAGGACCTGAAG
SerAlaLeuProAspTyrAlaSerGlnProGlyLysProProArgGluAspLeuLys
```

The arrows respectively separate the $V_H$, linker, $V_L$, and PE40 regions

TABLE 2

CYTOTOXICITY ($ID_{50}$) OF ANTI-TAC(Fv)-PE40 ON VARIOUS CELL LINES

| Cell Line | Anti-Tac(Fv)-PE40 ng/ml | PE ng/ml |
|---|---|---|
| HUT-102 | 0.15 | 10 |
| OVCAR-3 | >1000 | 30 |
| KB | >1000 | 60 |
| A431 | >1000 | 4 |
| CEM | >1000 | 200 |
| Cr.II.2 | 2.7 | Not done |

Cell lines OVCAR3, KB and A431 were seeded at $1\times10^5$/ml in 24-well plates one day prior to the addition of toxin. HUT-102 and CEM were washed twice and seeded at $3\times10^5$/ml in 24 well plates (also see FIG. 3). Various dilutions of toxin preparations were added, and 20 hours later the cells were labeled for 1.5 hr with $^3$H-leucine. The radioactivity in the TCA precipitate of the cells was determined. $ID_{50}$ is the concentration of toxin that inhibits protein synthesis by 50% as compared to a control with no toxin added. All the assays were done in duplicate and repeated three times.

What is claimed is:

1. A construct comprising DNA segments which direct the synthesis of a recombinant fusion protein in a suitable expression vector, wherein said fusion protein is a scFv-PE40.

2. A procaryotic or eucaryotic cell transformed or transfected with the construct of claim 1.

3. The construct of claim 1, wherein said construct directs the synthesis of a single chain polypeptide.

4. A procaryotic or eucaryotic cell transfected or transformed with the construct of claim 3.

5. The construct of claim 3, wherein said scFv is anti-Tac(Fv).

6. The construct of claim 5, wherein said DNA segments are contained in a plasmid.

7. The construct of claim 6 comprising plasmid of ATCC No. 67913.

8. The construct of claim 5, wherein said construct directs the synthesis of a fusion protein that is more cytotoxic than identical non-recombinant protein.

9. The construct of claim 5, wherein coding sequences for heavy chain variable domain is followed by coding sequences for light chain variable domain which is followed by the PE40 gene.

* * * * *